(12) United States Patent
Hull et al.

(10) Patent No.: US 7,209,223 B1
(45) Date of Patent: Apr. 24, 2007

(54) OPTICAL DEVICE FOR MEASURING OPTICAL PROPERTIES OF A SAMPLE AND METHOD RELATING THERETO

(75) Inventors: Matthew S Hull, Dublin, VA (US); Joshua P Averett, Radford, VA (US); Mark E Jones, Sequim, WA (US); Daniel R Klemer, Lexington, KY (US)

(73) Assignee: Luna Innovations Incorporated, Blacksburg, VA (US)

( * ) Notice: Subject to any disclaimer, the term of this patent is extended or adjusted under 35 U.S.C. 154(b) by 0 days.

(21) Appl. No.: 11/272,624

(22) Filed: Nov. 14, 2005

Related U.S. Application Data

(60) Provisional application No. 60/627,842, filed on Nov. 15, 2004.

(51) Int. Cl.
*G01N 21/64* (2006.01)
*G01N 21/59* (2006.01)

(52) U.S. Cl. .................. 356/73; 356/317; 356/318; 250/458.1

(58) Field of Classification Search ............ 356/73, 356/317, 318, 417; 250/458.1, 461.1
See application file for complete search history.

(56) References Cited

U.S. PATENT DOCUMENTS

| | | | |
|---|---|---|---|
| 3,649,833 A | 3/1972 | Leaf | |
| 3,754,145 A | 8/1973 | Leaf | |
| 4,105,334 A | 8/1978 | Halko et al. | |
| 5,477,322 A | 12/1995 | Webster | |
| 6,057,163 A | 5/2000 | McMillan | |
| 6,121,053 A | 9/2000 | Kolber et al. | |
| 6,558,958 B1 | 5/2003 | Pilevar et al. | |
| 6,683,314 B2 * | 1/2004 | Oostman et al. | 250/461.2 |
| 2002/0034457 A1 | 3/2002 | Reichert et al. | |
| 2003/0058440 A1 * | 3/2003 | Scott et al. | 356/318 |

OTHER PUBLICATIONS

Opti-Sciences, Inc., "Portable Fluorometer & Spectometer," Sep. 27, 2004, website page www.optisci.com/fsp2.htm.

* cited by examiner

*Primary Examiner*—F. L. Evans
(74) *Attorney, Agent, or Firm*—Joy L. Bryant

(57) ABSTRACT

A device and method for measuring optical properties of a sample are provided. The device comprises a housing surrounding a flow-through flow-cell having a sample inlet positioned proximate to a first end of the flow-cell and a sample outlet positioned proximate to a second end of the flow-cell and a sample chamber positioned between the sample inlet and the sample outlet. A plurality of excitation sources are positioned on the housing and are incident on a sample in the flow-cell. At least one excitation source has a wavelength that is different from the other excitation sources. At least one fluorescence emission detector, which detects a continuous broadband spectrum of emission wavelengths, is positioned in an operable relationship to the flow-cell. At least one signal interrogation system, which interprets a continuous fluorescence emission spectrum, is positioned in an operable relationship with each detector.

32 Claims, 10 Drawing Sheets

OPTICAL DEVICE FOR MEASURING OPTICAL PROPERTIES OF A SAMPLE AND METHOD RELATING THERETO

CROSS-REFERENCE TO RELATED APPLICATIONS

This application claims the benefit of U.S. Provisional Patent Application Ser. No. 60/627,842, entitled, "Optical Device for Measuring Optical Properties of a Sample and Method Relating Thereto," filed Nov. 15, 2004, which is hereby incorporated by reference in its entirety.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Contract No. NA03NOS4730220 awarded by the National Oceanic and Atmospheric Administration.

FIELD OF THE INVENTION

The present invention is related to optical devices used to measure optical changes in a sample. In particular, it relates to devices that measure fluorescence emissions of a sample.

BACKGROUND OF THE INVENTION

Marine biotoxins and harmful algae are a significant and expanding threat to human health and fisheries resources throughout the US. Five human illnesses are associated with toxic algae and consumption of seafood contaminated by harmful algae blooms (HAB) toxins: paralytic, neurotoxic, amnesic, and diarrhetic shellfish poisoning (called PSP, NSP, ASP, and DSP, respectively), and ciguatera fish poisoning (CFP). In addition to the adverse human health effects, whales, porpoises, seabirds, and other marine animals can become victims as well, accumulating algal toxins through the food chain by ingesting contaminated zooplankton or fish. Problems associated with harmful algal blooms have increased considerably in recent years, due in part to the simultaneous expansion of the fish-farming industry. Virtually every coastal state in the United States has reported recurring major blooms of harmful algae.

Optical devices are useful for analyzing optical changes in a sample that is found in a complex environment, such as the ocean. Such devices are particularly useful in identifying particular types of algae or other materials that fluoresce or absorb light. In general, either the absorbance or the fluorescence of a sample is measured and then interrogated to detect individual plant pigments. However, these approaches fail to discriminate a wide-range of plant pigments, missing critical information needed for the spectral characterization of water.

Leaf in U.S. Pat. No. 3,649,833 discloses a self-contained submersible fluorometer designed for the continuous in situ recording of concentrations of materials in an aqueous environment. The instrument can either be towed behind a moving boat or placed at rest in a flowing stream with the faired nose portion of the instrument facing the current. The pressure difference between an intake duct and an outlet duct causes water to flow through a transparent cuvette. A curved duct carries the water sample to and from the cuvette. A filter passes light from an excitation source which emits radiation at wavelengths which excite the sample material, whose concentration is to be detected, to fluoresce. As the material fluoresces, a filter that is selected to pass only those wavelengths of light from the desired fluorescent light to a photodetector. By continuously plotting the output of a potentiometer, vertical and horizontal profiles of material concentrations can be obtained for use in circulation and dilution studies. In particular, if the concentration of phytoplankton is to be determined, one need only replace the excitation filter with a filter that passes radiation over those wavelengths which excite chlorophyll to fluorescence. An emission filter is selected to pass those wavelengths characteristic of fluorescing chlorophyll. A photodetector is selected to be sensitive to all the wavelengths under consideration. That is, in making concentration measurements the photodetector is sensitive to the wavelengths emitted by the excitation lamp as well as the wavelengths which pass through the emission filter. The output from the photodetector passes through a bandpass filter-amplifier to produce an input to a synchronous detector. An integrator acts to integrate the output from the detector to produce a waveform. The problem with this approach is that the configuration of the device does not allow for the collection of data over a continuous range of wavelengths. Nor does it provide for the use of multiple excitation sources. Rather, the output from the photodetector corresponding to the light from the optical fiber increases in response to the detection of an increase in fluorescence of the sample material. As the intensity of light in the balancing path increases, the intensity difference in the two arms of the bridge decreases causing decay in the waveform. Hence the data collected is for a discrete wavelength rather than a continuous range of wavelengths.

Opti-Sciences, Inc. have disclosed a portable fluorometer and spectrometer on its website www.optisci.com/fsp2.htm. The device is capable of measuring fluorescence and absorbance in the same instrument. A standard configuration comes equipped with both a fluorometer and a spectrometer module. However, it also functions as a stand alone spectrometer or fluorometer. The instrument can also be equipped with application specific filters (up to 5 excitation and 6 emissions) for multi-fluorescence analysis. This device differs from that of the present invention because it is limited to testing at a discrete wavelength rather than over a continuous range of wavelengths. Nor does the device allow for multiple excitation sources.

An object of the present invention is to provide a device and method for measuring optical properties in a sample where the device generates a continuous fluorescence emission spectrum.

Another object of the present invention is to provide a device and method for measuring optical properties over a range of wavelengths.

Another object of the present invention is to provide a device that is capable of detecting fluorescence, absorbance, or fluorescence and absorbance simultaneously.

SUMMARY OF THE INVENTION

By the present invention, a device and method for measuring optical properties of a sample are provided. The device comprises a housing surrounding a flow-through flow-cell. The flow-cell has a sample inlet positioned proximate to a first end of the flow-cell and a sample outlet positioned proximate to a second end of the flow-cell. A sample chamber is positioned between the sample inlet and the sample outlet. A plurality of excitation sources are positioned on the housing in an operable relationship to the sample chamber. At least one excitation source has a wavelength that is different from the other excitation sources. Each excitation source is incident on a sample in the flow-cell. At least one fluorescence emission detector is positioned in an operable relationship to the flow-cell. The fluorescence emission detector detects a continuous broadband spectrum of emission wavelengths emitted from the sample upon excitation by each excitation source. At least one signal interrogation system is positioned in an operable relationship with each detector. The signal interrogation system interprets a continuous fluorescence emission spectrum. The device may also incorporate at least one absorbance detector for measuring transmitted power that is spectrally dependent on the absorbance characteristics of the sample.

In practicing the method of the present invention, the optical device described above is provided. The device is exposed to a fluid sample. The fluid sample is then exposed to a plurality of light excitations. Fluorescence emissions of the sample over a plurality of wavelengths are detected and a continuous wavelength spectrum is produced.

The advantage of the present invention over the prior art is that it allows for either fluorescence, absorbance, or the simultaneous detection of fluorescence and absorbance to be achieved upon exposure of a sample to multiple wavelengths of light. Moreover, because a continuous broadband spectrum of emission wavelengths emitted from the sample upon excitation are detected and interpreted, the user is not limited to emission data distributed over discrete wavelengths. Hence, the user does not need to have prior knowledge with respect to the wavelength at which a particular sample fluoresces. Because of these unique features, the present invention is useful as a continuous monitor for phytoplankton (e.g., harmful algae), relaying information real-time.

Additional objects and advantages of the invention will be set forth in part in the description which follows, and in part, will be obvious from the description, or may be learned by practice of the invention. The objects and advantages of the invention will be obtained by means of instrumentalities in combinations particularly pointed out in the appended claims.

BRIEF DESCRIPTION OF THE DRAWINGS

The accompanying drawings illustrate a complete embodiment of the invention according to the best modes so far devised for the practical application of the principals thereof, and in which.

DETAILED DESCRIPTION OF THE PREFERRED EMBODIMENTS

Figure 1:
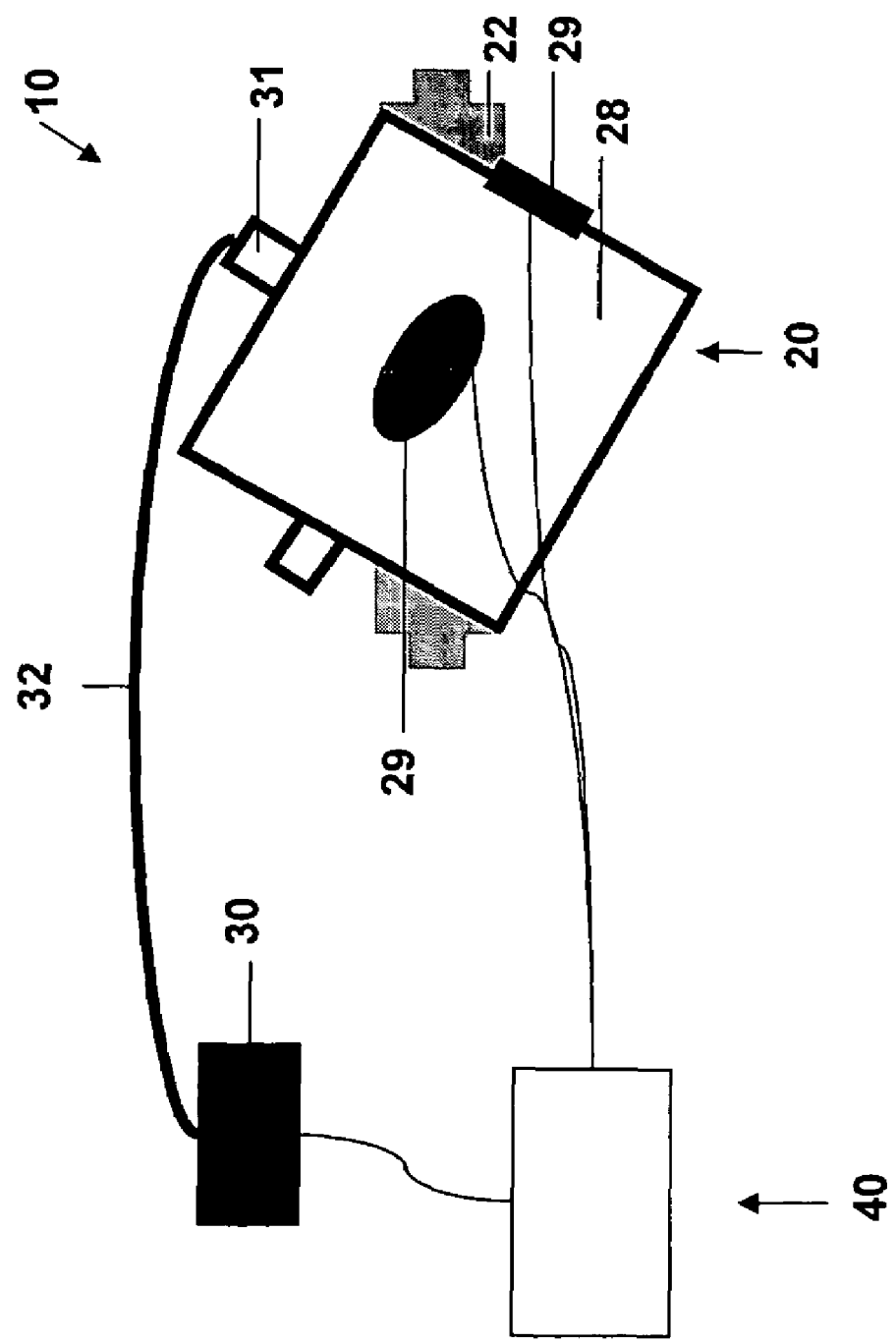
FIG. 1 depicts a simple embodiment of the device of the present invention.

Referring now to the drawings where similar parts are labeled the same throughout, FIG. 1 depicts an embodiment of the device of the present invention. Simply defined, the device 10 has two general components: a sample cell 20 and at least one signal interrogation system 40. The device measures optical properties of a sample and, preferably, is a spectrofluorometer. The sample cell 20 comprises a flow-through flow-cell 22 disposed within a housing 28. By flow-through it is meant that the sample cell permits continuous passive flow-through sampling of a sample. This configuration makes the devices of the present invention well suited for in situ operation on autonomous vehicles. In addition, the two-component configuration permits interfacing various types of low-cost sample cells (e.g., with different light sources, detectors, flow-cells, etc.) with a single greater-cost signal interrogation system. Hence, the system is very versatile.

Figure 2:
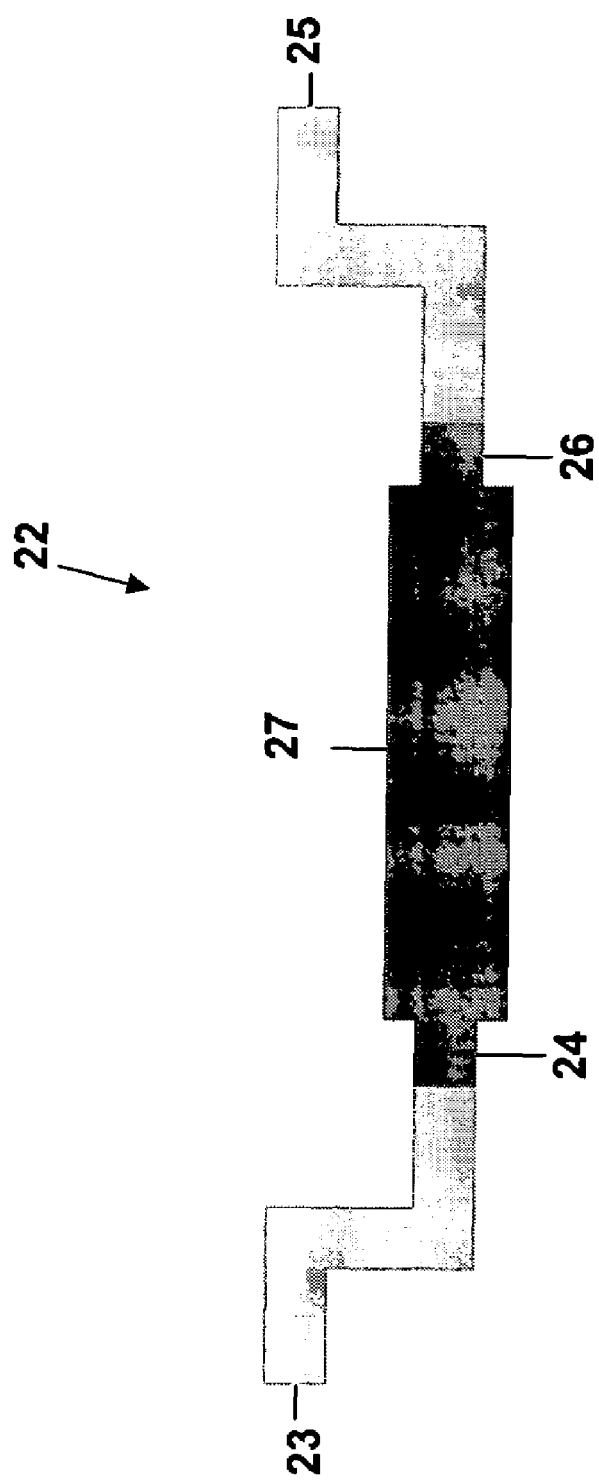
FIG. 2 depicts a preferred flow-cell embodiment of the present invention.

FIG. 2 depicts a preferred flow-cell configuration for the present invention. The flow-cell 22 has a sample inlet 23 positioned proximate to a first end 24 of the flow-cell 22. A sample outlet 25 is positioned proximate to a second end 26 of the flow-cell 22. A sample chamber 27 is positioned between the sample inlet 23 and the sample outlet 25. The fluid path for the sample chamber 27 is preferably shaped or designed in such a way that none of the sample can escape until the sample chamber 27 is completely full. This minimizes bubbling that may cause distortions in the emission spectrum. The preferred flow-cell allows for passive fluidic handling, meaning that the fluid sample moves through the sample chamber, permitting mid-stream sampling. Most preferably, the flow-cell has the configuration of that known as a Fluorometer Cell which is commercially available from Starna Cells, Inc. in Atascadero, Calif.

Figure 3:
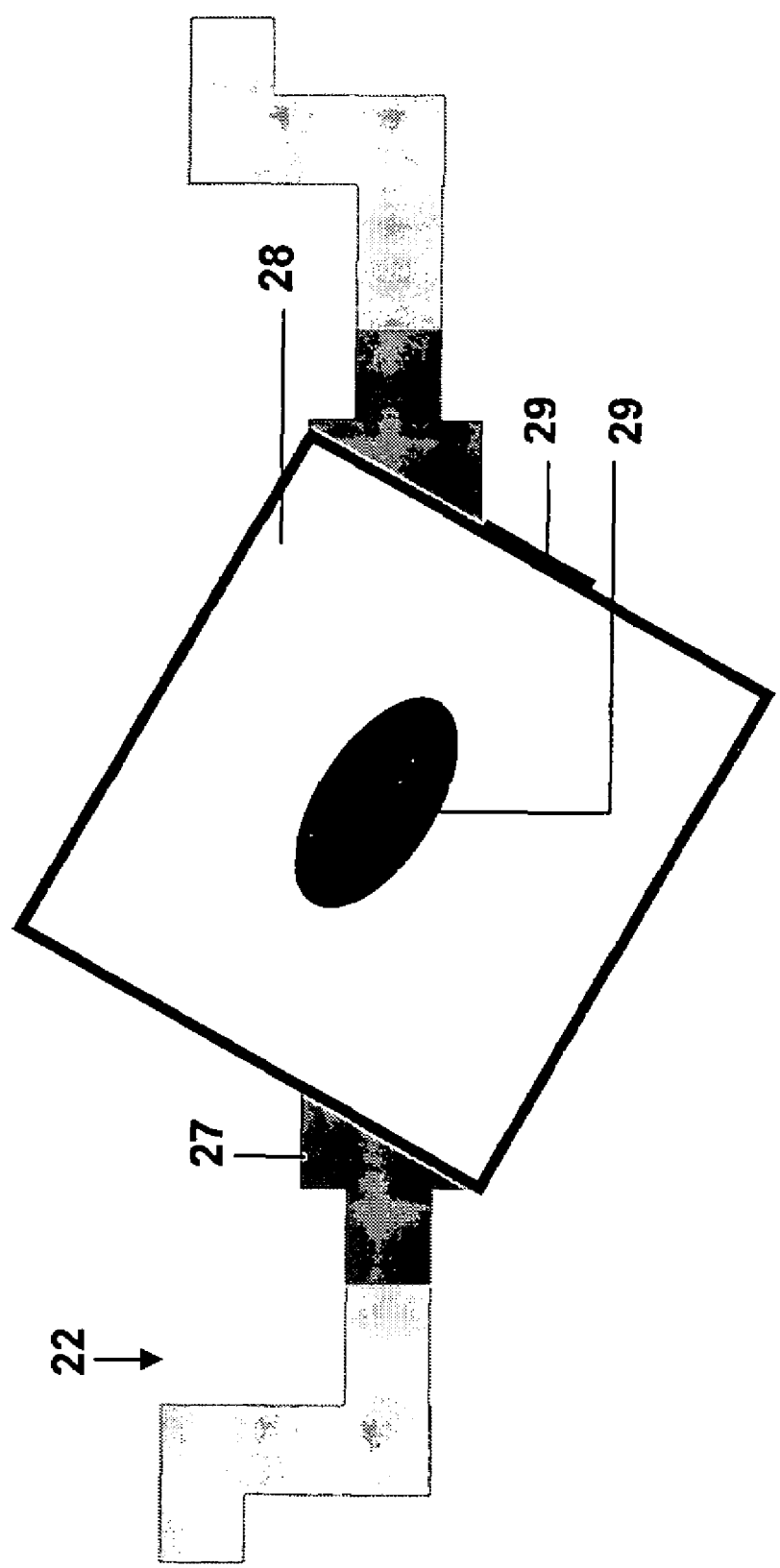
FIG. 3 depicts a preferred housing configuration of the present invention.

Referring now to FIG. 3, a preferred embodiment of the housing 28 is shown. The housing 28 surrounds the flow-cell 22. A plurality of excitation sources 29 are positioned on the housing 28 in an operable relationship to the sample chamber 27 such that each excitation source is incident on a sample in the flow-cell 22. Any excitation source known to those of ordinary skill in the art may be employed. Preferably, each excitation source is selected from the group consisting of: a narrowband source and a broadband source. The narrowband source is preferably selected from the group consisting of: a laser diode, a strobe laser diode, a laser, and a bandpassed broadband source. Most preferably, the narrowband source is a strobe laser diode. The broadband source is preferably selected from the group consisting of: a light emitting diode, a xenon lamp, a deuterium lamp, and an inert gas lamp. Most preferably, the broadband source is a light emitting diode such as Shark™ which may be purchased from Opto Technology, Inc. in Wheeling, Ill. At least one excitation source has a wavelength that is different from the other excitation sources. Alternatively, each excitation source has a different wavelength and causes a different excitation of the sample.

Figure 4:
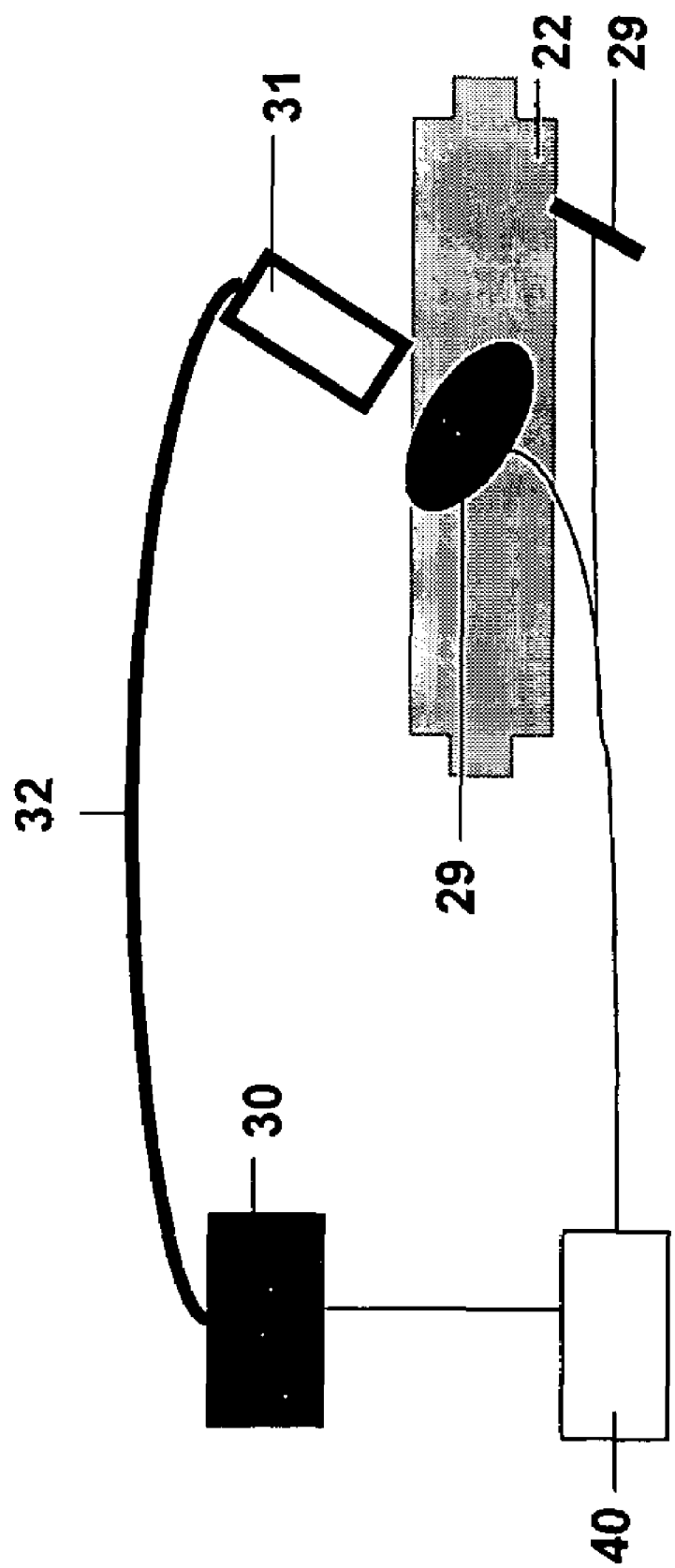
FIG. 4 depicts a preferred configuration of the fluorescence emission detector.

Referring back to FIG. 1, at least one fluorescence emission detector 30 is positioned in an operable relationship to the flow-cell 22. The fluorescence emission detector 30 detects a continuous broadband spectrum of emission wavelengths emitted from the sample upon excitation by each excitation source 29. Any fluorescence emission detector known to one of ordinary skill in the art may be employed in the present invention. FIG. 1 depicts a preferred embodiment where the fluorescence emission detector 30 is optically linked to a fiber optic probe assembly 31 through a means for collecting fluorescence emission optical signals 32 that is connected to the fiber optic probe assembly 31 (see FIG. 4). FIG. 4 depicts the fiber optic probe assembly 31 positioned in an orthoganol relationship to the flow-cell 22 and the excitation sources 29. This relationship permits orthoganol fluorescence emission wavelength measurements and absorbance measurements to be made. A preferred fiber optic probe assembly is commercially available and sold as RoMack from RoMack, Inc. in Williamsburg, Va. In a preferred embodiment, each fluorescence emission detector 30 is optically linked to a fiber optic probe assembly 31 through a means for collecting fluorescence emission optical signals 32. Examples of such means include: a large core multi-mode fiber bundle; a small core multi-mode fiber bundle; a lens/fiber combination; a fiber-bundle combination; and a single large core multi-mode fiber. Most preferably, this means is a small core multi-mode fiber bundle.

Referring to FIGS. 1 and 4, at least one signal interrogation system 40 is positioned in an operable relationship to the fluorescence emission detector 30 wherein the signal interrogation system 40 interprets a continuous fluorescence emission spectrum. This spectrum differs from that of the prior art because it takes into consideration the width and the shape of the curve. The wavelength and intensity vary depending on the sample, hence wavelengths ranging from about 100–1500 nm may be detected. The signal interrogation system 40 preferably comprises a user input means for controlling activation of each excitation source. An example of such means is a computer equipped with command/control software that activates each excitation source, causing the sample to fluoresce as it passes through the sample chamber. In addition, the signal interrogation system comprises an interpretive software means for transferring an optical signal from each detector to a computer. Preferably, the signal interrogation system comprises a means for interpreting spectral peak width and intensity.

Figure 5:
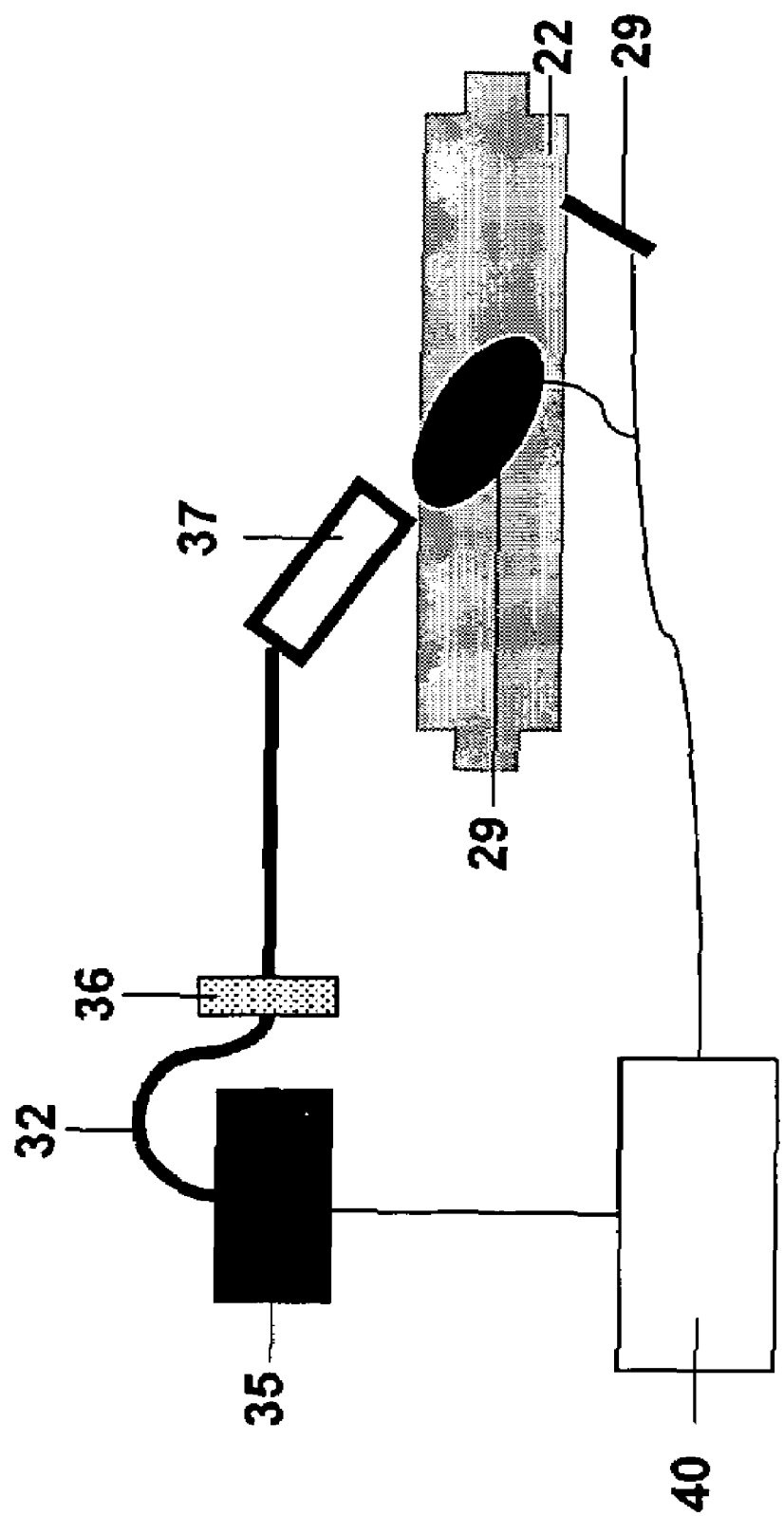
FIG. 5 depicts a preferred configuration of the absorbance detector.

In an alternative embodiment of the invention, shown in FIG. 5, at least one absorbance detector 35 is positioned in an operable relationship to a fiber optic probe assembly 37 which is positioned in an operable relationship to at least one excitation source 29. The absorbance detector 35 detects both absorbance and fluorescence at individual wavelengths. Hence, narrowband excitations are detected as the sample absorbs light from the excitation source(s). Simply stated, the absorbance detector measures transmitted power that is spectrally dependent on absorbance properties of the sample. When it is desirable to filter for a specific wavelength, at least one optical filter 36 is positioned in an operable relationship to the absorbance detector 35. Each absorbance detector 35 has a means 32 for collecting absorbance optical signals detected by the fiber optic probe assembly 37. Each means is selected from the group consisting of: a photodiode; a large core multi-mode optical fiber bundle; a small core multi-mode optical fiber bundle; a lens/optical fiber combination; an optical fiber-bundle combination; and a single large core multimode optical fiber. Preferably, the means is a fiber bundle. A signal interrogation system 40 comprises a user input means for controlling activation of each excitation source and interpretive software means for transferring an optical signal from each detector 35 to a computer. Preferably, the signal interrogation system 40 comprises a means for interpreting spectral peak width and intensity.

Figure 6:
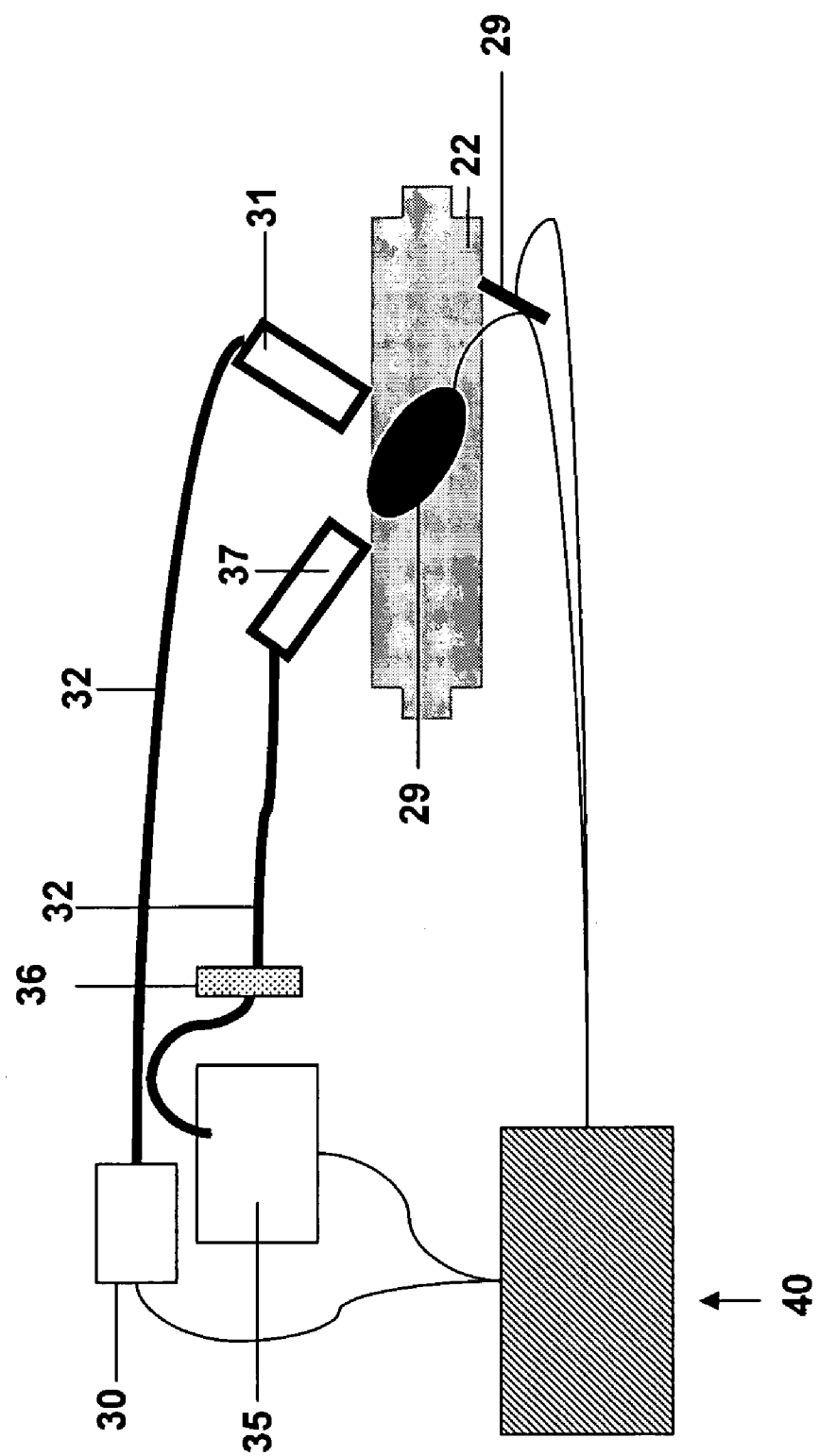
FIG. 6 depicts an embodiment of the invention employing both a fluorescence and an absorbance detector.

FIG. 6 depicts another embodiment of the invention where both a fluorescence detector 30 and an absorbance detector 35 are used in combination. In this embodiment, a fiber optic probe assembly for measuring fluorescence 31 is positioned in an orthoganol relationship to the flow-cell 22 such that orthoganol fluorescence emission wavelength measurements are made as the sample is exposed to the excitation sources 29. A separate fiber optic probe assembly for measuring absorbance 37 is also positioned in an orthoganol relationship to the flow-cell 22 such that orthoganol absorbance emission wavelength measurements are made as a sample is exposed to the excitation sources 29. When it is desirable to filter for a specific wavelength, at least one optical filter 36 is positioned in an operable relationship to the absorbance detector 35. Each fiber optic probe assembly is optically connected 32 to its respective absorbance detector 35 or fluorescence emission detector 30. A signal interrogation system 40 comprises a user input means for controlling activation of each excitation source 29 and an interpretive software means for transferring an optical signal from each detector 30, 35 to a computer. The signal interrogation system 40 preferably further comprises a means for interpreting spectral peak width and intensity.

In practicing the method of the present invention, the device is used to measure fluorescence alone, absorbance alone, or fluorescence and absorbance in combination. In general, the method comprises the steps of providing an optical device comprising a plurality of excitation sources incident on a sample contained in a flow-cell. At least one excitation source has an excitation wavelength that is different from the other excitation sources. At least one detector is positioned in an operable relationship to the flow-cell. The detector is either a fluorescence emission detector or an absorbance detector. Preferably, the detector is a fluorescence emission detector. Alternatively, the detector is a fluorescence emission detector in combination with at least one absorbance detector. This combination permits simultaneous detection of fluorescence and absorbance by a sample. The detector is positioned in an operable relationship to a fiber optic probe assembly and detects a continuous broadband spectrum of excitation emission wavelengths produced by the sample upon exposure to each excitation source. At least one signal interrogation system is positioned in an operable relationship with each detector. The signal interrogation system measures a continuous wavelength spectrum.

In practice, the device is exposed to a fluid sample. Hence, the device is actually submerged in the fluid sample rather than the fluid sample being injected into the flow-cell of the device. Preferably, the fluid sample is selected from the group consisting of: a biological sample; a chemical sample; and a liquid sample. Most preferably the fluid sample is a biological sample such as algae.

The sample is exposed to a plurality of light excitations. In a preferred embodiment, these light excitations are autonomously switched. The autonomous switching between the plurality of light excitations may occur individually or in combination. Such switching occurs by using command/control software that activates each of the excitation sources which then fluoresces a sample as it passes through the sample chamber of the flow-cell. The software allows the user to regulate the drive current, sampling interval and firing sequence of the excitation sources.

After the sample has been exposed to a plurality of light excitations, optical responses of the sample are detected over a plurality of wavelengths such that a continuous wavelength spectrum is produced. Additionally, the spectral peak width and shape are interpreted.

EXAMPLES

Example 1

A machined housing containing multiple light emitting diodes (LEDs), a flow cell, and a fiber optic probe assembly was fabricated. A cube-like housing having four flat windows was fabricated by machining a piece of aluminum such that a square slot is positioned in the center of the housing. The square slot securely seats a 10-mm square cuvette or a 13-mm test tube or other sample holder. The sample holder is a flow-through, passive, non-power sampling device such as the Starna flow cell, commercially available from Starna. A RoMack Fiber assembly with a customized SMA end fitting, flange, and a PVC monocoil or flexible stainless steel jacket was coupled to the housing. The fiber assembly was customized to place the end of a 1000 micron core fiber in close proximity to the optically-clear flow-through chamber. The coupling that joins the assembly to the housing is easily removed to permit rapid change-out of various configurations (e.g., fibers of varying core size and length) of optical fiber assemblies. Four LED sources were used as the excitation sources. Examples of various LEDs include the Luxeon™ LED, Shark™ LED, and UFO™ LED. Each is commercially available from Optotech. The excitation sources are removable such that different types and different combinations of LEDs are employed. This design permits flexibility in the device to use different excitation sources and permits switching between wavelengths.

Example 2

The housing of Example 1, was integrated into a spectrometer-based fluorometer that was used in an environmentally controlled shipboard laboratory. The housing design was integrated with an Ocean Optics USB-S2000 spectrometer that had a 253–842 nm grating. The housing was linked to the spectrometer through a fiber-bundle link. As a sample entered the device at the inlet tube, it passed through the sample chamber, and exited through the sample outlet tube. Command/control software activated each of the LEDs which then fluoresces a sample as it passed through the sample chamber. The fiber bundle transferred the optical emission spectra from the sample to the spectrometer. Built-in interpretive software transferred the optical signal to a shipboard PC.

Example 3

Figure 7A:
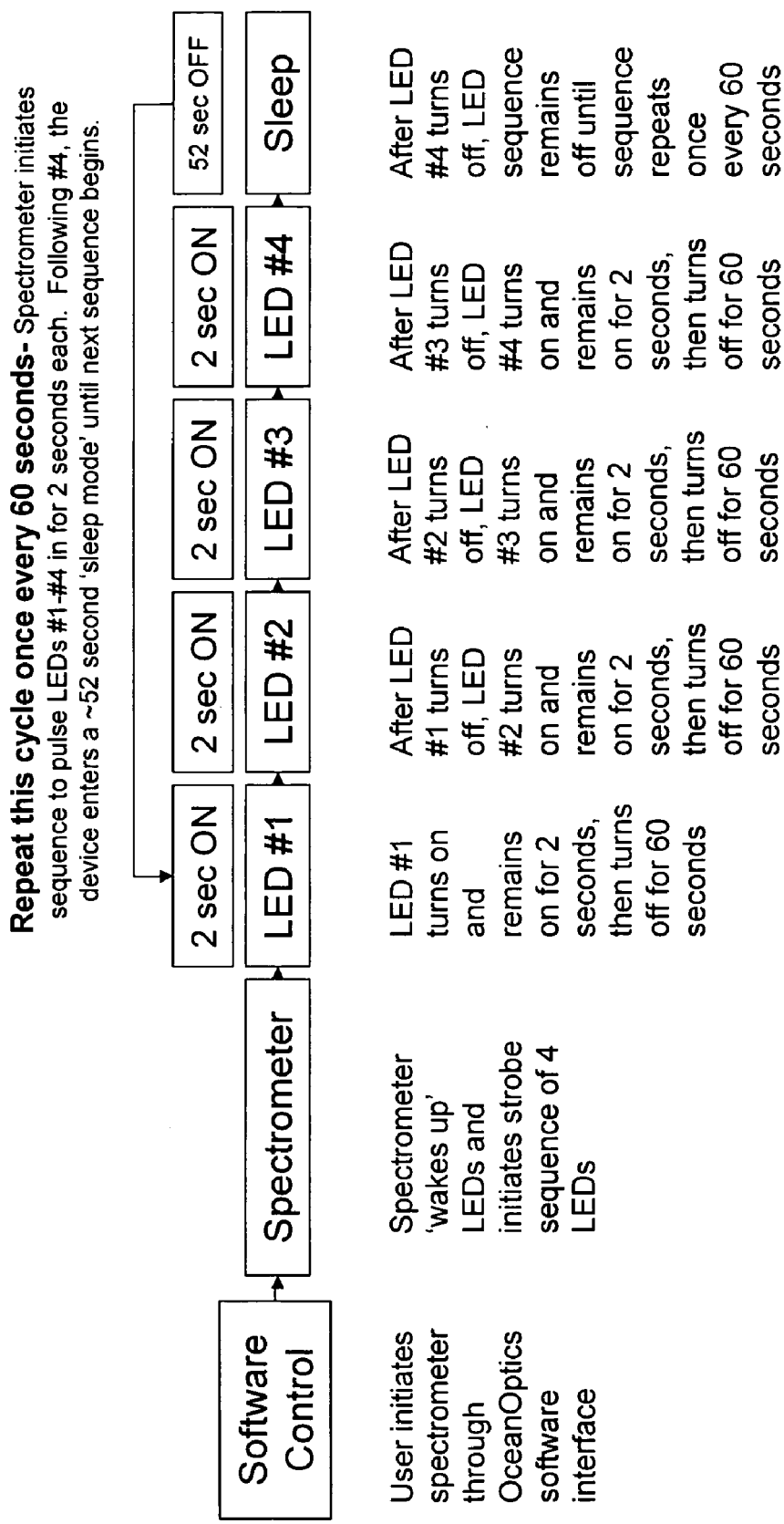
FIG. 7A depicts a sampling sequence employed for the present invention.
Figure 7B:
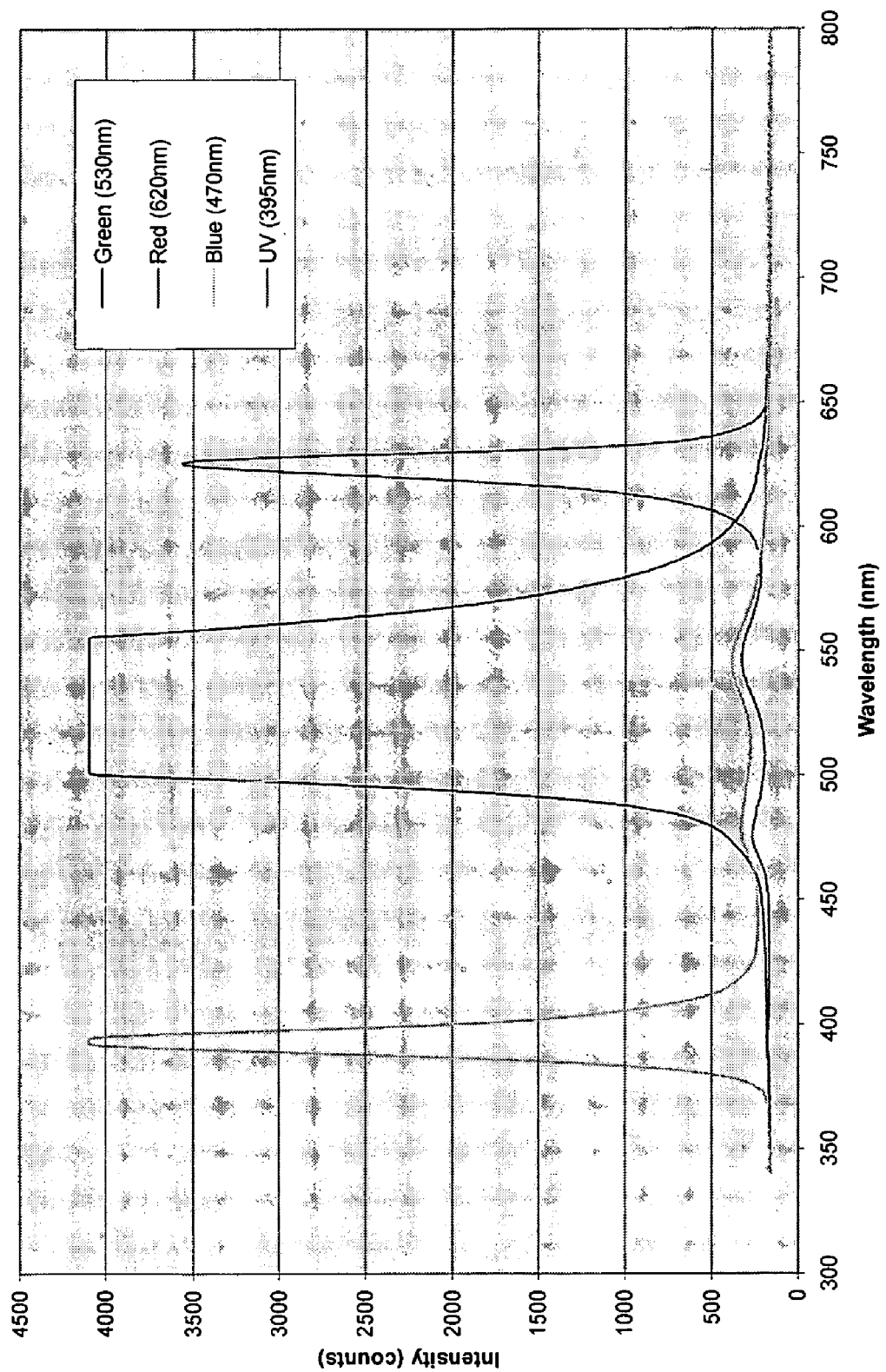
FIG. 7B is a plot of continuous spectrum showing simultaneous operation for a plurality of excitation sources.

Various sampling sequences may be used with the device. For example, FIG. 7A depicts a sampling sequence that was employed with the device. In this example, the system "wakes up" and drives 4 LED sources in a pre-determined sequence. This approach minimizes power requirements, thus demonstrating the versatility of the device for use on autonomous, in situ platforms (e.g. buoys, autonomous vehicles). The spectral output for this type of sequence is shown in FIG. 7B. This plot is of a continuous spectrum showing simultaneous operation of a plurality of excitation sources.

Example 4

Figure 8:
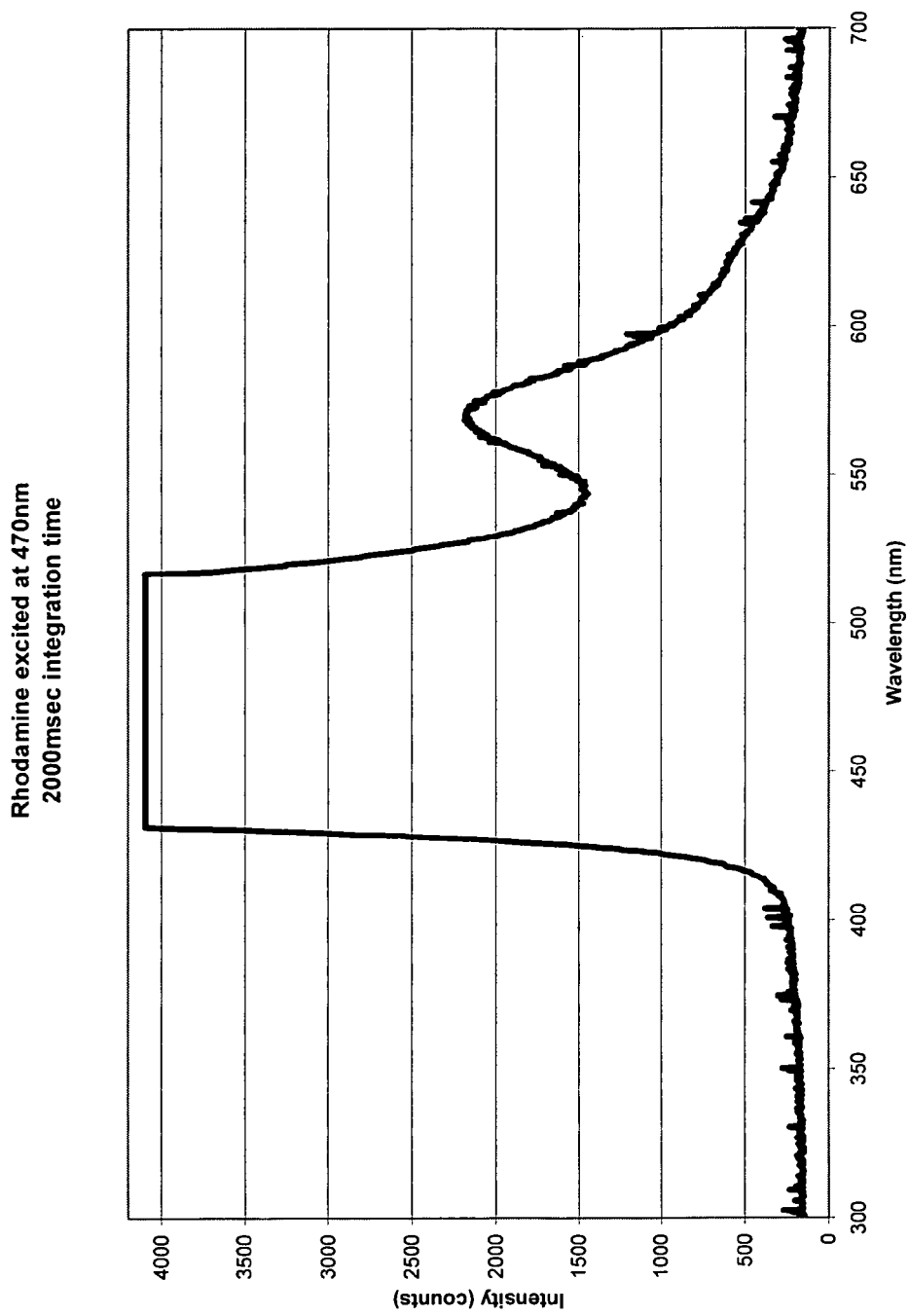
FIG. 8 is an emission spectra for a rhodamine dye standard using a 470 nm LED with an integration time of 2000 msec.

Rhodamine dye standards were used as a control to evaluate the function of the device. FIG. 8 shows the continuous fluorescence emission spectrum when rhodamine dye was excited using a single 470 nm Shark™ LED. Operation of the LED is verified by the presence of an excitation peak at 470 nm. A clear emission peak is observed at 575 nm, thus indicating the fluorescent emission of the rhodamine dye. For simplicity, this graph shows excitation of rhodamine by only a single source. It is important to note, however, that the device permits use of multiple excitation sources in various sampling configurations also (as shown in FIG. 7A).

Example 5

Figure 9:
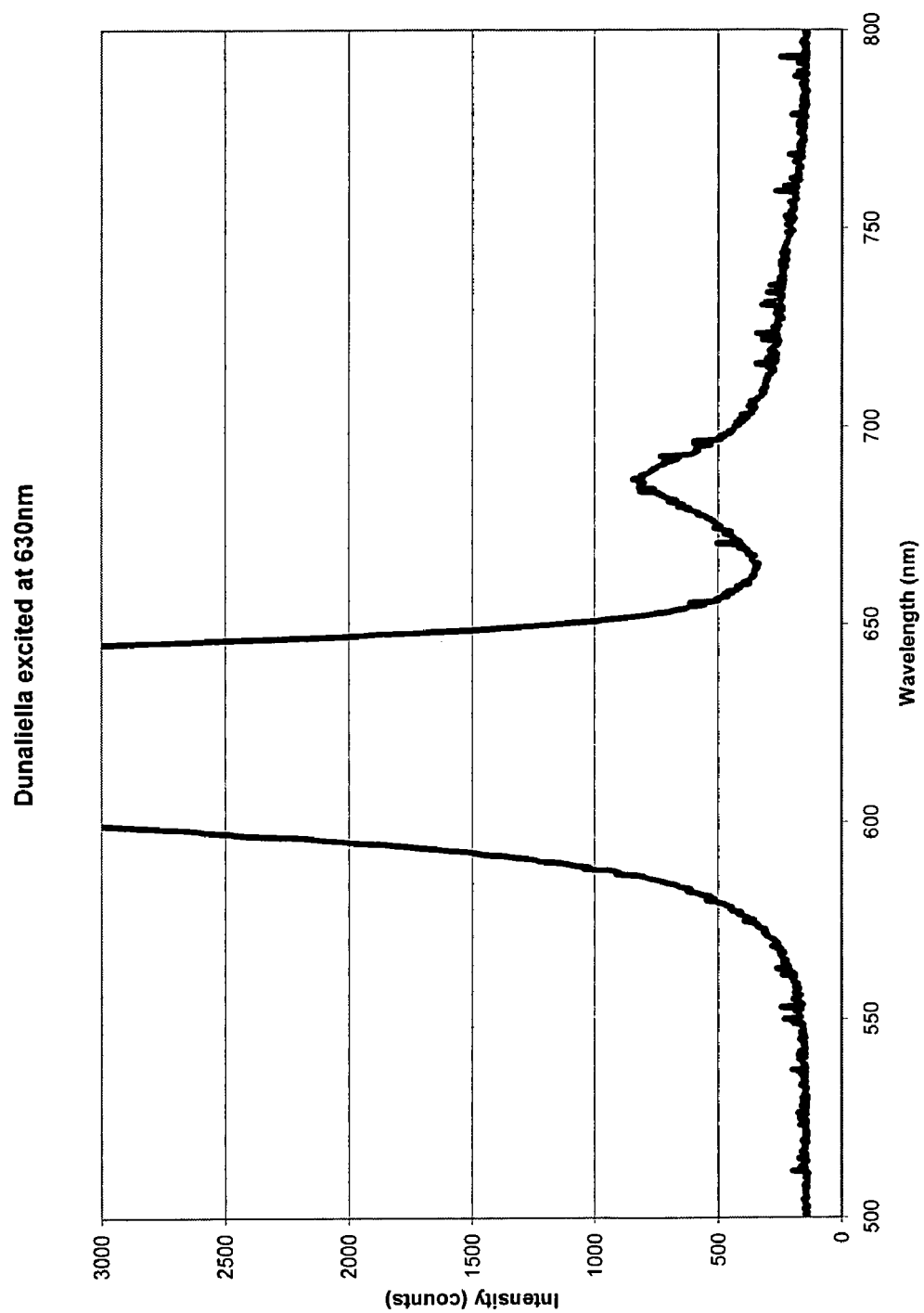
FIG. 9 is an emission spectra for a pure culture of *Dunaliella* excited at 630 nm at a 2000 msec integration time.

Actual phytoplankton samples were excited by wavelengths of light known to produce emission spectra. FIG. 9 shows the emission spectrum for a pure culture of *Dunaliella* excited at 630 nm for an integration time of 2000 msec. This spectrum clearly indicates the chlorophyll emission peak, which is known to occur at 685 nm, and reduces to practice the use of the device of the present invention for exciting phytoplankton samples and subsequently recording the continuous fluorescence emission spectra of those samples. For simplicity, FIG. 9 shows excitation of *Dunaliella* by only a single source. It is important to note, however, that the device permits use of multiple excitation sources in various sampling configurations also (as shown in FIG. 7A).

The above description and drawings are only illustrative of preferred embodiments which achieve the objects, features and advantages of the present invention, and it is not intended that the present invention be limited thereto. Any modification of the present invention which comes within the spirit and scope of the following claims is considered part of the present invention.

What is claimed is:

1. A device for measuring optical properties of a sample, the device comprising:
   a housing;
   a flow-through flow-cell disposed within the housing, the flow-cell having a sample inlet positioned proximate to a first end of the flow-cell, a sample outlet positioned proximate to a second end of the flow-cell, and a sample chamber therebetween;
   a plurality of excitation sources positioned on the housing in an operable relationship to the sample chamber wherein at least one excitation source has an excitation wavelength that is different from the other excitation sources and wherein each excitation source is incident on a sample in the flow-cell;
   at least one fluorescence emission detector positioned in an operable relationship to the flow-cell wherein the fluorescence emission detector detects a continuous broadband spectrum of emission wavelengths emitted from the sample upon excitation by each excitation source; and
   at least one signal interrogation system positioned in an operable relationship with each detector wherein the signal interrogation system interprets a continuous fluorescence emission spectrum.

2. A device according to claim 1, further comprising at least one absorbance detector positioned in an operable relationship to each excitation source wherein the absorbance detector measures transmitted power that is spectrally dependent on light absorbed by the sample.

3. A device according to claim 1, wherein the fluorescence emission detector is a fiber optic probe assembly positioned in an orthoganol relationship to the flow cell and the excitation sources.

4. A device according to claim 2, wherein the fluorescence emission detector is a fiber optic probe assembly positioned in an orthoganol relationship to the flow cell wherein orthoganol fluorescence emission wavelength measurements are made.

5. A device according to claim 1, wherein each excitation source is selected from the group consisting of: a narrowband source and a broadband source.

6. A device according to claim 5, wherein the narrowband source is selected from the group consisting of: a laser diode, a strobe laser diode, a laser, and a bandpassed broadband source.

7. A device according to claim 6, wherein the narrowband source is a strobe laser diode.

8. A device according to claim 5, wherein the broadband source is selected from the group consisting of: a light emitting diode, a xenon lamp, a deuterium lamp, and an inert gas lamp.

9. A device according to claim 8, wherein the broadband source is a light emitting diode.

10. A device according to claim 1, wherein each excitation source is a narrowband source and wherein each fluorescence emission detector is a broadband detector.

11. A device according to claim 1, wherein each excitation source has a different wavelength and causes a different excitation of the sample.

12. A device according to claim 2, further comprising at least one optical filter positioned in an operable relationship to the absorbance detector wherein each optical filter is designed to filter for a specific wavelength.

13. A device according to claim 1, wherein each fluorescence emission detector has a means for collecting fluorescence emission optical signals and wherein each means is selected from the group consisting of: a large core multi-mode fiber bundle; a small core multi-mode fiber bundle; a lens/fiber combination; a fiber-bundle combination; and a single large core multi-mode fiber.

14. A device according to claim 13, wherein the means for collecting fluorescence emission optical signals is a small core multi-mode fiber bundle.

15. A device according to claim 2, wherein each absorbance detector has a means for collecting absorbance optical signals and wherein each means is selected from the group consisting of: a photo diode; a large core multi-mode fiber bundle; a small core multi-mode fiber bundle; a lens/fiber combination; a fiber-bundle combination; and a single large core multi-mode fiber.

16. A device according to claim 15, wherein the means for collecting absorbance optical signals is a fiber-bundle combination.

17. A device according to claim 1, wherein the signal interrogation system comprises a user input means for controlling activation of each excitation source.

18. A device according to claim 2, wherein the signal interrogation system comprises a user input means for controlling activation of each excitation source.

19. A device according to claim 1, wherein the signal interrogation system comprises an interpretive software means for transferring an optical signal from each detector to a computer.

20. A device according to claim 19, wherein the signal interrogation means comprises a means for interpreting spectral peak width and intensity.

21. A device according to claim 2, wherein the signal interrogation system comprises an interpretive software means for transferring an optical signal from each detector to a computer.

22. A device according to claim 21, wherein the signal interrogation means comprises a means for interpreting spectral peak width and intensity.

23. A method for measuring optical properties of a sample, the method comprising the steps of:
  a) providing an optical device wherein the optical device comprises a plurality of excitation sources incident on a sample contained in a flow-cell wherein at least one excitation source has an excitation wavelength that is different from the other excitation sources;
  at least one detector positioned in an operable relationship to the flow-cell wherein the detector detects a continuous broadband spectrum of excitation emission wavelengths produced by the sample upon exposure to each excitation source; and
  at least one signal interrogation system positioned in an operable relationship with each detector wherein the signal interrogation system measures a continuous wavelength spectrum;
  b) exposing the device to a fluid sample;
  c) exposing the sample to a plurality of light excitations; and
  d) detecting optical responses of the sample over a plurality of wavelengths wherein a continuous wavelength spectrum is produced.

24. A method according to claim 23, wherein the detector is either a fluorescence emission detector or an absorbance detector.

25. A method according to claim 23, wherein the detector is a fluorescence emission detector.

26. A method according to claim 25, wherein the detector further comprises at least one absorbance detector.

27. A method according to claim 26, wherein fluorescence and absorbance of the sample are detected simultaneously.

28. A method according to claim 23, wherein the fluid sample is selected from the group consisting of: a biological sample; a chemical sample; and a liquid sample.

29. A method according to claim 28, wherein the fluid sample is a biological sample.

30. A method according to claim 23, wherein the plurality of light excitations are autonomously switched.

31. A method according to claim 30, wherein the autonomous switching between the plurality of light excitations occurs individually.

32. A method according to claim 30, wherein the autonomous switching between the plurality of light excitations occurs in combination.

* * * * *